United States Patent [19]

Bigler et al.

[11] Patent Number: 5,383,242
[45] Date of Patent: Jan. 24, 1995

[54] ELECTRIC TOOTHBRUSH

[75] Inventors: Michael Bigler, Ittigen; Edgar Hommann, Grossaffoltern, both of Switzerland; Scott Myerly, Alpheretta, Ga.

[73] Assignee: Bausch & Lomb Incorporated, Rochester, N.Y.

[21] Appl. No.: 98,977

[22] Filed: Jul. 28, 1993

[30] Foreign Application Priority Data

Jan. 8, 1992 [DE] Germany ............... 4225548

[51] Int. Cl.⁶ .................. A61C 17/34; A46B 13/02
[52] U.S. Cl. ........................................ 15/22.1; 74/57
[58] Field of Search ............. 15/22.1, 22.2, 22.4; 74/57; 310/50

[56] References Cited

U.S. PATENT DOCUMENTS

| | | | |
|---|---|---|---|
| 764,470 | 7/1904 | Jones et al. | 74/57 |
| 793,587 | 6/1905 | Johnson . | |
| 1,134,047 | 3/1915 | Hunter | 74/57 |
| 1,476,433 | 12/1923 | Vandervoort . | |
| 1,712,579 | 5/1929 | Nichols . | |
| 1,792,358 | 2/1931 | Byers et al. | 15/22.2 |
| 1,869,991 | 8/1932 | White et al. . | |
| 1,945,616 | 2/1934 | Mastrud | 15/22.1 |
| 2,044,863 | 6/1936 | Sticht . | |
| 2,140,307 | 12/1938 | Belaschk et al. . | |
| 2,201,190 | 5/1940 | Mastrud . | |
| 3,104,405 | 9/1963 | Perrinjaquet . | |
| 3,160,902 | 12/1964 | Aymar . | |
| 3,400,417 | 9/1968 | Moret et al. . | |
| 3,489,936 | 1/1970 | Boyles . | |
| 3,562,566 | 2/1971 | Kircher . | |
| 3,577,579 | 5/1971 | Duve et al. . | |
| 4,156,620 | 5/1979 | Clemens . | |
| 4,274,173 | 6/1981 | Cohen . | |
| 4,408,623 | 10/1983 | Murray | 15/22.1 |
| 4,756,202 | 7/1988 | Kawamoto . | |
| 4,783,869 | 11/1988 | Lee . | |
| 4,827,550 | 5/1989 | Graham et al. . | |
| 4,974,278 | 12/1990 | Hommann . | |
| 4,989,287 | 2/1991 | Scherer . | |
| 5,142,723 | 9/1992 | Lustig et al. | 15/22.1 |

FOREIGN PATENT DOCUMENTS

| | | |
|---|---|---|
| 0221460 | 5/1987 | European Pat. Off. . |
| 0254397 | 1/1988 | European Pat. Off. . |
| 0357863 | 2/1989 | European Pat. Off. . |
| 706260 | 5/1931 | France . |
| 2268854 | 5/1978 | France . |
| 2578408 | 9/1986 | France ............ 15/22.1 |
| 524651 | 5/1931 | Germany . |
| 2736286 | 12/1978 | Germany . |
| 2838015 | 3/1979 | Germany . |
| 1632386 | 4/1980 | Germany . |
| 2940275 | 4/1981 | Germany . |
| 333481 | 4/1985 | Germany . |
| 334165 | 5/1985 | Germany . |
| 3544256 | 6/1987 | Germany . |

OTHER PUBLICATIONS

Muller, Prof. Dr. J., *Basic Terms of Deviations in CAM Gears*, U. of Rostock, Dept. of Agricultural Engineering, Report No. 11 of the KDT Working Group on CAM Gears.

Primary Examiner—Edward L. Roberts
Attorney, Agent, or Firm—Denis A. Polyn; Salvatore P. Pace; Katherine McGuire

[57] ABSTRACT

An electric toothbrush having in its slip-on brush a piston is disclosed, which is set rotating by a motor shaft projecting out of the handle segment. This piston exhibits a lifting cam, by means of which it effects an axial motion relative to the motor shaft in the slip-on brush. This axial motion causes a reciprocating motion of a toothed rack, which sets the bristle tufts of the toothbrush rotating.

24 Claims, 3 Drawing Sheets

ELECTRIC TOOTHBRUSH

BACKGROUND OF THE INVENTION

The invention relates to an electric toothbrush with an electric motor, which generates a motion of rotation and has a motor shaft, a gear that converts the motion of rotation into a reciprocating stroke, and a slip-on brush, which is to be attached to a handle segment so as not to be rotatable in said handle segment and which has a reciprocatable toothed rack in order to drive the rotatable bristle carriers.

Such an electric toothbrush is the subject matter of the EP-B-O 254 397. In the case of the toothbrush known in this document a contrate gear, which is driven by means of a pinion by the electric motor in the handle segment, is disposed in an eccentric, from which a crank arm leads to a reciprocatable connecting rod that leads out of the handle segment. This connecting rod couples with a toothed rack in the slip-on brush, when said brush is slid on the handle segment. The toothed rack generates in turn an alternating motion of rotation of the individual bristle carriers in the brush head.

If one wants to attain an adequately long stroke of the toothed rack, so that the bristle tufts exert more than one rotation at each stroke, the connecting rod leading out of the handle segment must execute an equally long stroke. That requires an eccentric, which is offset on the contrate gear by half the stroke. The result is automatically a relatively large diameter of the contrate gear, so that the diameter of the handle segment, too, must be correspondingly large, a feature that is often undesired.

The problem on which the invention is based is to design an electric toothbrush of the aforementioned kind in such a manner that its gear can be arranged to convert the motion of rotation of the electric motor into a reciprocating motion even while generating a longer stroke in toothbrushes with a small diameter.

SUMMARY OF THE INVENTION

This problem is solved by the invention in that the gear exhibits a piston, which is connecting to the toothed rack, is aligned in the longitudinal direction of the toothbrush, and can be put into a revolving motion of rotation by the electric motor and which can be set oscillating back and forth by means of a closed, revolving lifting cam and a guiding pin, which interacts with said lifting cam; or by means of the revolving lifting cam, which is provided in said guiding pin, a component, which engages with said lifting cam and is connected to the toothed rack, is set oscillating.

Such a gear has a small space requirement in the radial direction of the toothbrush, even if a large stroke has to be generated with it, because this stroke is generated by the course of the lifting cam; and the desired stroke can be generated exclusively by extending the lifting cam in the axial direction or by arranging several lifting cams in succession. Despite this advantage, the toothbrush according to the invention is constructed very simply, so that it can be manufactured inexpensively and the risk of malfunctioning is low. The lifting cam can be provided either in the shell of the piston or in kinematic reverse in the inner shell of a borehole bearing the piston.

An especially advantageous embodiment of the invention consists of the gear being disposed in the slip-on brush and the piston having a coupling, which, when the slip-on brush is slid on, couples with a drive journal, which leads out of the handle segment and is set into a revolving motion of rotation by the electric motor.

With this design, which is possible, first of all, due to the small size of the gear of the invention in the radial direction, the goal is reached that the gear, which has a tendency to wear, is no longer disposed in the handle segment. Thus, this gear is replaced automatically, when the slip-on brush is replaced. Such a replacement of the slip-on brush takes place in any event from time to time, because the bristles are subject to wear due to the use of the toothbrush. Another advantage of this embodiment lies in the fact that only a rotating journal and not a reciprocating journal has to project from the handle segment. During a longer stroke of a reciprocating journal, there is the risk of injury due to this journal when the slip-on brush is not slipped on.

A very simple design of the gear consists of the piston being axially moveable on the motor shaft and axially moveable in the housing of the handle segment or the slip-on brush; and the lifting cam being designed to generate a reciprocating motion of the piston; and the toothed rack being coupled axially with the piston.

The gear can be further simplified if the lifting cam is a guide groove that extends on the outer shell of the piston and with which engages a guide pin, which is permanently attached to the housing. With too great a lifting cam pitch, the gear could automatically lock. This can be avoided without the need for intersecting lifting cams, if the piston has on its side facing away from the electric motor an extension of the piston with a second lifting cam, on which a toothed rack holder engaging with the second lifting cam can be moved axially and cannot be rotated relative to the housing. With such an embodiment the piston generates by means of its stroke a first part of the stroke of the toothed rack; and the toothed rack holder generates by means of a stroke relative to the piston another part of the stroke of the toothed rack.

Especially with the arrangement of the gear in a slip-on brush it is advantageous if the extension of the piston has a smaller diameter than the piston, because the cross section of the slip-on brush usually decreases towards the front and can, therefore, accommodate the extension of the piston whose diameter is decreased.

The toothbrush hold can be ensured not to rotate in a simple manner in that the outer shell of the toothed rack holder has at least one radial guide pin, which engages with a longitudinal groove of the housing of the toothbrush or the slip-on brush; said groove extending in the direction of the stroke.

An alternative possibility to increase the stroke without a larger lifting cam pitch or crossing of the lifting cam regions consists of the piston exhibiting on the side facing away from the electric motor a coaxial guide bore, into which the toothed rack with the journal projects; this journal exhibiting a second lifting cam, which engages with the guide bore; and the toothed rack exhibiting a locking mechanism.

The toothed rack can be ensured not to rotate in a simple manner in that it is formed by a pin, which penetrates radially through the piston outside the guide bore and whose two ends reach into a longitudinal groove that is attached stationarily to the housing.

Another possibility to generate a longer stroke with a small lifting cam pitch consists of the lifting cam of the piston leading one and one-half times around the piston and then back to its starting pat. Such an embodiment leads to an intersecting lifting cam.

If one wants to dispense with the stroke of the piston, a stroke of the toothed rack can also be achieved in that the piston is mounted so as to be immovable; and a connecting rod, which is connected to the toothed rack, engages with its lifting cam.

Two toothed racks move counter clockwise, when two separate connecting rods, each of which is connected to a toothed rack, engage with the lifting cam.

Even the piston, to be coupled with the motor shaft, can be adjusted to the decrease in diameter of the slip-on brush in the direction of the head of the bristles, when the piston is designed as a truncated cone.

The invention permits numerous embodiments. To further illustrate its basic principle, several embodiments are shown as schematic drawings and are described as follows.

DETAILED DESCRIPTION OF THE INVENTION

Figure 1:
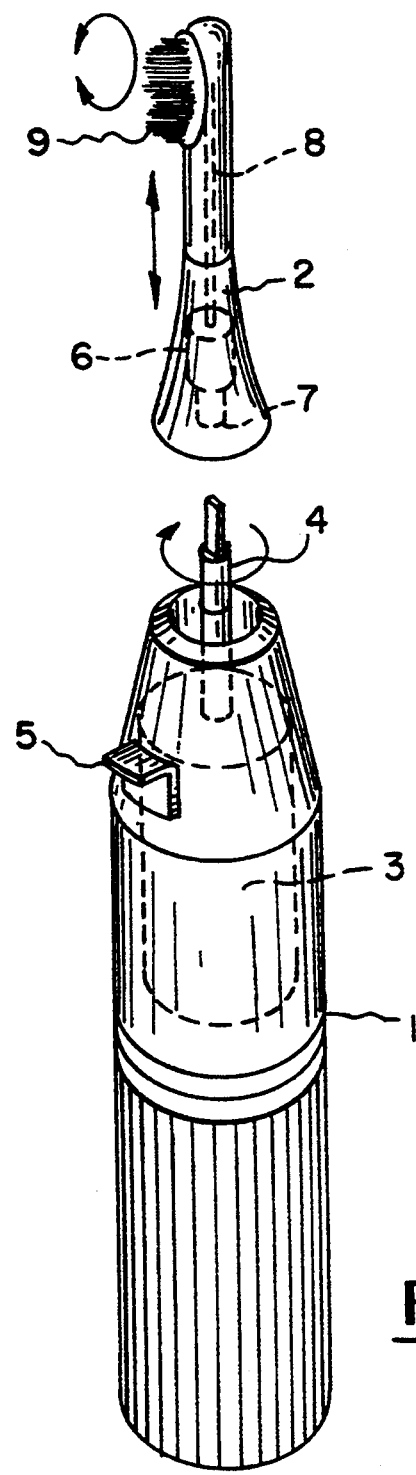
FIG. 1 is a perspective view of an electric toothbrush according to the invention with the slip-on brush not slid on yet.

FIG. 1 shows an electric toothbrush, which comprises substantially a handle segment 1 and a slip-on brush 2. The handle segment 1 has an electric motor 3, which is shorn as a dashed line and which can set a motor shaft 4, protruding from the handle segment 1, into a constant motion of rotation. A switch 5 on the outside of the handle segment 1 serves the purpose of switching the electric motor 3 on and off.

The slip-on brush 2 has a gear 6 that is also shown with a dashed line and that has a coupling 7, which, when slipping the slip-on brush 2 on the handle segment 1, couples with the motor shaft 4. The gear 6 is designed in such a manner that it can generate a reciprocating motion of a toothed rack 8 on the basis of the motion of rotation introduced by the motor shaft 4. This toothed rack can set the bristle carriers (not shown) with bristle tuft 9 rotating so as to alternate from left to right, for example in the exact identical manner as the toothed rack according to the EP-B-O 254 397.

It should be noted that the gear 6 is always arranged in the slip-on brush 2 in FIG. 1 and in all subsequent Figures. However, it is also possible to provide this gear 6 in the handle segment 1. Then, instead of a revolving motor shaft 4, a reciprocating ram, which couples with the toothed rack 8 in the handle segment 1, must be led out of the handle segment 1.

Figure 2:
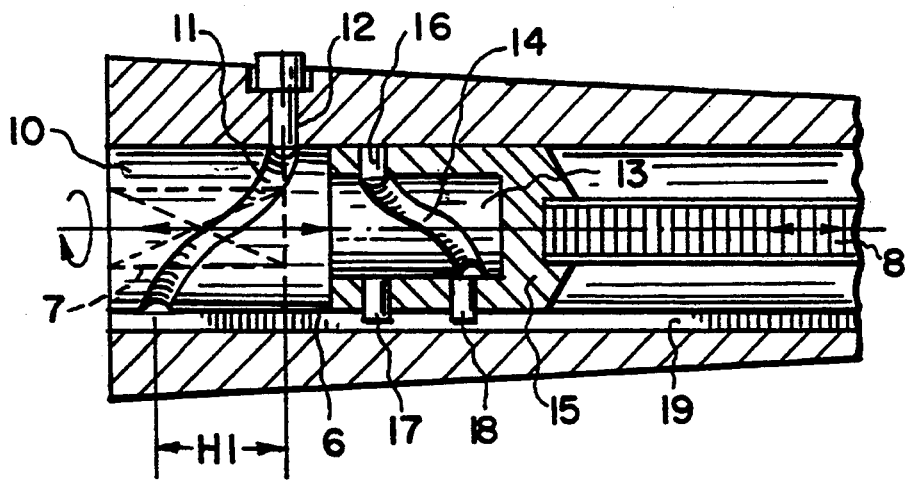
FIG. 2 is a longitudinal view of a first embodiment of a gear of the invention that is disposed in a slip-on brush.

FIG. 2 is a longitudinal view of a subregion of the slip-on brush 2 with the gear 6 and the toothed rack 8 on a significantly enlarged scale. This gear 6 has a piston 10, whose outer shell exhibits a lifting cam 11 designed as a peripheral groove. Into this lifting cam 11 projects a guide pin 12, which is guided through the housing of the slip-on brush 2 and is, thus, attached stationarily. If the motor shaft 4, shown in FIG. 1, engages with the coupling 7 of the piston 10 and drives it thus so as to rotate, then the piston 10 executes a stroke H1 determined by the pitch of the lifting cam 11. Assumed is that the piston 10 is mounted axially moveably on the motor shaft 4 and in the slip-on brush 2.

The piston 10 has on its side, facing away from the coupling 7 and thus the electric motor 3, a piston extension 13, whose diameter is smaller and whose shell has a second revolving lifting cam 14, that is oriented in the opposing direction. A toothed rack holder 15, which is designed as a cylindrical sleeve and which is connected securely to the toothed rack 8 and engages with this lifting cam 14 by means of a cam 16, is slipped on the piston extension 13.

The outer shell of the toothed rack holder 15 has two guide pins 17, 18, which are directed radially outwardly and which engage with a longitudinal groove 19 of the housing of the slip-on brush 2, said groove extending in the direction of stroke. In this manner the toothed rack holder 15 cannot rotate, but can be moved axially.

When the piston 10 with its piston extension 13 rotates and it effects the already explained stroke H1, then the piston extension 13 also rotates within the toothed rack holder 15. The consequence is that the toothed rack holder 15 moves back and forth on the piston extension 13 relative to the piston 10 and it moves increasing further from the piston 10. This stroke adds to the stroke of the piston 10, so that the toothed rack 8 makes a correspondingly larger stroke than the piston 10.

Figure 3:
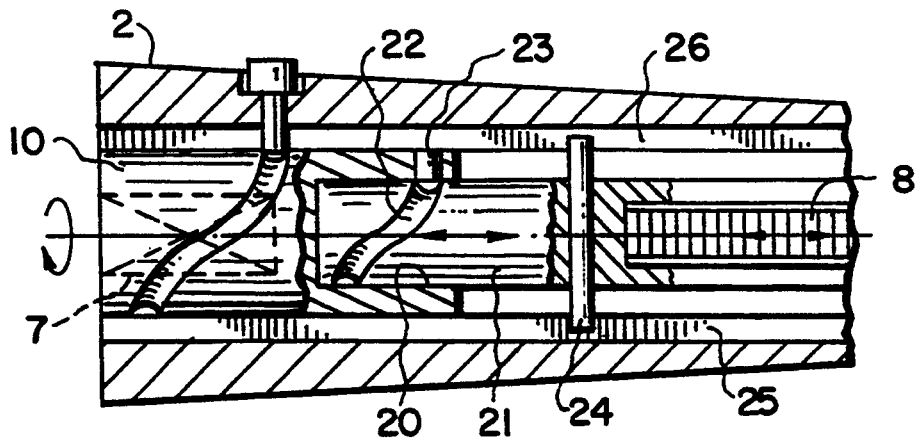
FIG. 3 is a longitudinal view of a second embodiment of a gear of the invention that is disposed in a slip-on brush.

The embodiment accordingly to FIG. 3 represents virtually a kinematic reverse of the embodiment according to FIG. 2. In this embodiment, just as in the embodiment according to FIG. 2, in the handle segment 1 the piston is provided with the coupling 7. However, it has no piston extension, but rather has on the side facing away from the coupling 7 a coaxial guide bore 20, into which the toothed rack 8 projects with a journal 21. The shell of this journal 21 has a lifting cam 22, with which a radially inwardly directed cam 23 of the piston 10 engages. A pin 24, which is guided radially through the journal 21 outside the guide bore 20 and engages on both sides of the journal 21 with a longitudinal groove 25, 26 of the housing of the slip-on brush 2, serves the purpose of ensuring that piston 10 does not twist.

If in the case of the embodiment according to FIG. 3 the piston 10 effects its combined stroke and rotation, then the journal 21 moves due to the second lifting cam 22 and cam 23 of the journal 21 within the guide bore 20, so that the toothed rack 8 effects a stroke that is greater than that of the piston 10.

Figure 4:
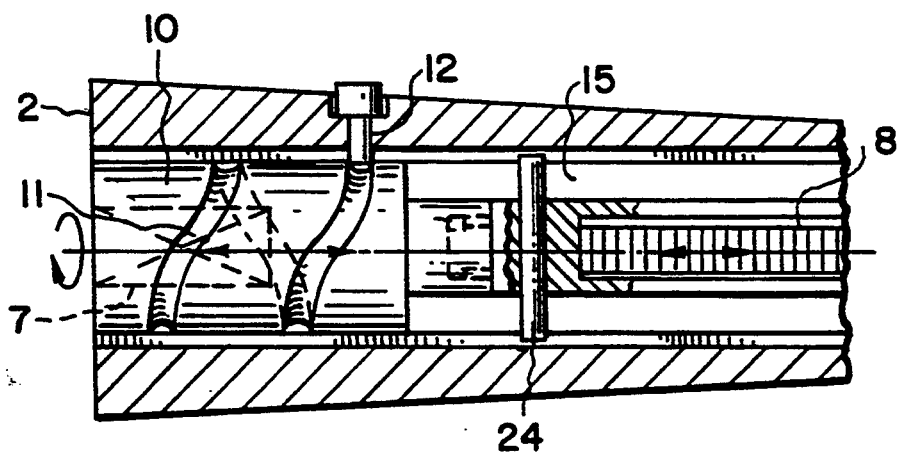
FIG. 4 is a longitudinal view of a third embodiment of a gear-of the invention that is disposed in a slip-on brush.

In the embodiment according to FIG. 4 the revolving lifting cam 11 rotates one and one-half times around the piston 10 and correspondingly moves back again to its starting point. The consequence is that due to the revolution of the piston 10 the piston effects a greater stroke than in the case of the two embodiments described above, the lifting cam 11 exhibiting an intersecting point on the side (not evident from FIG. 4). In this embodiment the toothed rack 8 is connected in turn by means of the pin 4 to the toothed rack holder 15, which, however, cannot effect a relative motion to the piston 10, so that the toothed rack 8 always effects precisely the same stroke as the piston 10.

Figure 5:
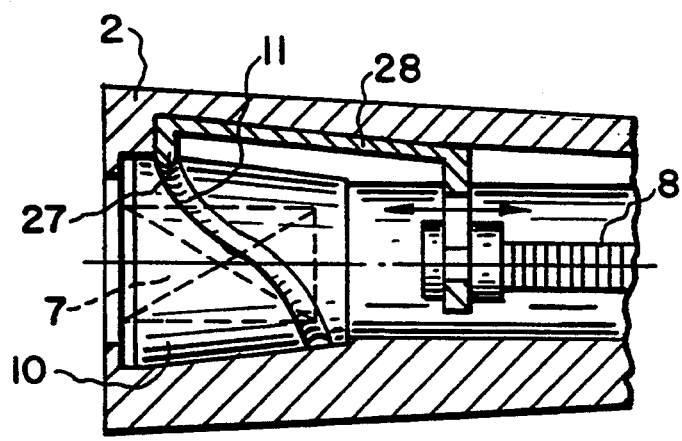
FIG. 5 is a longitudinal view of a fourth embodiment of a gear of the invention that is disposed in a slip-on brush.

In the embodiment according to FIG. 5, the piston 10 is designed as a truncated cone. It tapers in the direction of the side of the brush head (not illustrated), thus in FIG. 5 to the right. In contrast to the embodiment described previously, the piston 10 in the slip-on brush 2, according to FIG. 5, can be only rotated, not, however, moved axially. In its revolving lifting cam 11, a cam follower 27 of a connecting rod 28, whose end facing away from the coupling 7, is connected securely to the toothed rack 8.

If the piston 10 is set rotating by means of the motor shaft 4 shown in FIG. 1, then the connecting rod 28 moves back and forth in accordance with the course of the lifting cam 11, thus to the right and the left, as seen in FIG. 5. Since it is connected to the toothed rack 8, said toothed rack effects a corresponding motion. It should be noted that the piston 10 does not have to be a truncated cone for the explained function. The shape of a truncated cone was chosen only because the slip-on brush normally tapers in the direction of the head of the brush and the truncated cone shape is, therefore, especially space saving.

Figure 6:
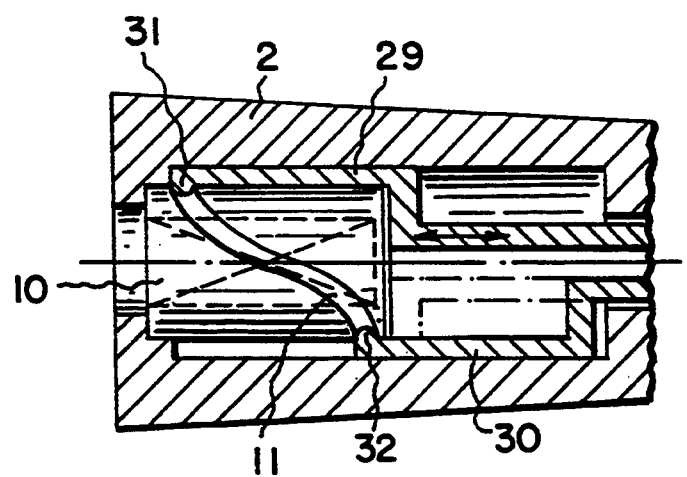
FIG. 6 is a longitudinal view of a fifth embodiment of a gear of the invention that is disposed in a slip-on brush.

In the embodiment according to FIG. 6, two connecting rods 29, 30, and one cam follower 31, 32 each engage with the lifting cam 11 of the piston 10. The points of engagement are offset by 180° based on the revolving motion of the piston 10. In this manner the connecting rod 29 is situated precisely in its position pointing usually to the left, when the connecting rod 30 has moved the furthest to the right. The two connecting rods 29, 30 can drive two toothed racks (not illustrated).

We claim:

1. A cleaning device defining a longitudinal axis therethrough, the cleaning device comprising:
   (a) a housing:
   (b) a motor shaft within the housing and aligned substantially parallel to the longitudinal axis;
   (c) a motor located in the housing for rotating the shaft about the longitudinal axis of the shaft;
   (d) a reciprocable rack located in the housing which extends substantially parallel to the longitudinal axis of the cleaning device;
   (e) a cleaning head operatively connected with the reciprocable rack;
   (f) a gear mounted for rotation with the shaft and for sliding movement along the shaft, the gear being operatively connected to the reciprocable rack so as to convert the rotation of the shaft into a reciprocating stroke of the rack;
   (g) a lifting cam and a cam follower, one of the lifting cam and the cam follower positioned to rotate with the gear, the other of the lifting cam and the cam follower associated with the housing of the cleaning device, the cam follower interacting with the lifting cam such that when the gear is in the revolving motion of rotation, the gear oscillates back and forth along the shaft.

2. The cleaning device of claim 1, the housing further comprising:
   a handle segment for containing the motor; and
   a slip-on head segment which removably attaches to the handle segment.

3. The cleaning device of claim 2, wherein the gear is disposed in the slip-on head segment, and the gear has a coupling which, when the slip-on head segment is slid on the handle segment, couples with the motor shaft, which leads out of the handle segment.

4. The cleaning device of claim 1, wherein the lifting cam is a guide groove that extends on the outer surface of the gear and with which engages the cam follower, which is fixed to the housing of the cleaning device.

5. The cleaning device of claim 1, further comprising:
   an extension on the gear on the side of the gear facing away from the motor;
   a second lifting cam; and
   a second cam follower, one of the second lifting cam and the second cam positioned to rotate with the extension and the other of the second lifting cam and the second cam follower being associated with the reciprocable rack such that when the gear is rotating, the extension rotates and causes a corresponding reciprocating motion of the rack.

6. The cleaning device of claim 1, further comprising:
   a coaxial guide bore on the gear, the coaxial guide bore being located on the side of the gear facing away from the motor;
   a second lifting cam; and
   a second cam follower, one of the second lifting cam and the second cam follower being located in the guide bore, and the other of the second lifting and the second cam follower being associated with the reciprocable rack such that when the gear is rotating, the guide bore rotates and causes a corresponding reciprocating motion of the reciprocable rack.

7. The cleaning device of claim 1, wherein the lifting cam is a guide groove which extends at least one time around the gear and then back to its starting point, and the cam follower is fixed relative to the housing of the cleaning device.

8. The cleaning device of claim 1, wherein said cleaning device is an electric toothbrush.

9. A cleaning device defining a longitudinal axis therethrough, the cleaning device comprising:
   (a) a housing comprising:
      a handle segment; and
      a slip-on head segment removably attached to the handle segment;
   (b) a shaft extending from the handle segment to the head segment and aligned substantially parallel to the longitudinal axis;
   (c) a motor located in the handle segment for rotating the shaft about the longitudinal axis of the shaft;
   (d) a reciprocable rack located in the head segment which extends substantially parallel to the longitudinal axis of the cleaning device;
   (e) a cleaning head operatively connected with the reciprocable rack;
   (f) a gear disposed in the slip-on head segment for converting the rotation of the shaft into a reciprocating stroke for the reciprocable rack, the gear being oriented to rotate about the longitudinal axis of the cleaning device and being capable of rotation with the shaft;
   (g) a lifting cam on the outer periphery of the gear; and
   (h) a component which engages with the lifting cam and is connected to the reciprocable rack, whereby the rotation of the gear causes the component and the reciprocable rack to reciprocate back and forth.

10. The cleaning device of claim 9, wherein the gear is designed as a truncated cone.

11. The cleaning device of claim 9, further comprising:
   a second reciprocable rack which extends substantially parallel to the longitudinal axis of the cleaning device; and
   a second component which also engages with said lifting cam and is connected to the second reciprocable rack.

12. The cleaning device of claim 11, wherein said second component engages said gear at said lifting cam approximately 180° offset on said gear from where said first component engages said gear at said lifting cam.

13. The cleaning device of claim 9, wherein said cleaning device is an electric toothbrush.

14. The cleaning device of claim 9, wherein the gear has a coupling which, when the slip-on head segment is slid on the handle segment, couples with the motor shaft, which leads out of the handle segment.

15. A cleaning device defining a housing and a longitudinal axis therethrough, the cleaning device comprising:
   (a) a motor shaft aligned substantially parallel to the longitudinal axis;
   (b) a motor for rotating the shaft about the longitudinal axis of the shaft;
   (c) a reciprocable rack which extends substantially parallel to the longitudinal axis of the cleaning device;
   (d) a cleaning head operatively connected with the reciprocable rack;
   (e) a gear mounted for rotation with the shaft and for sliding movement along the shaft, the gear being operatively connected to the reciprocable rack so as to convert the rotation of the shaft into a reciprocating stroke of the rack;
   (f) a lifting cam and a cam follower, one of the lifting cam and the cam follower positioned to rotate with the gear, the other of the lifting cam and the cam follower associated with the housing of the cleaning device, the cam follower interacting with the lifting cam such that when the gear is in the revolving motion of rotation, the gear oscillates back and forth along the shaft;
   (g) an extension on the gear on the side of the gear facing away from the motor;
   (h) a second lifting cam; and
   (i) a second cam follower, one of the second lifting cam and the second cam positioned to rotate with the extension and the other of the second lifting cam and the second cam follower being associated with the reciprocable rack such that when the gear is rotating, the extension rotates and causes a corresponding reciprocating motion of the rack.

16. The cleaning device of claim 15, wherein the reciprocable rack is confined so as to not rotate relative to the housing of the cleaning device.

17. The cleaning device of claim 15, wherein the extension has a smaller diameter than the gear.

18. The cleaning device of claim 15, wherein the first lifting cam and the second lifting cam are oriented in opposing directions such that as the gear moves axially outward on the motor shaft relative to the motor, the reciprocable rack moves axially outward relative to the extension.

19. The cleaning device of claim 15, further comprising at least one radial guide pin associated with the reciprocable rack for movement therewith; and
   a longitudinal groove located in the housing of the cleaning device or the slip-on brush head assembly, the groove extending axially in the direction of the stroke of the reciprocable rack, the groove receiving the radial guide pin.

20. A cleaning device defining a housing and a longitudinal axis therethrough, the cleaning device comprising:
   (a) a motor shaft aligned substantially parallel to the longitudinal axis;
   (b) a motor for rotating the shaft about the longitudinal axis of the shaft;
   (c) a reciprocable rack which extends substantially parallel to the longitudinal axis of the cleaning device;
   (d) a cleaning head operatively connected with the reciprocable rack;
   (e) a gear mounted for rotation with the shaft and for sliding movement along the shaft, the gear being operatively connected to the reciprocable rack so as to convert the rotation of the shaft into a reciprocating stroke of the rack;
   (f) a lifting cam and a cam follower, one of the lifting cam and the cam follower positioned to rotate with the gear, the other of the lifting cam and the cam follower associated with the housing of the cleaning device, the cam follower interacting with the lifting cam such that when the gear is in the revolving motion of rotation, the gear oscillates back and forth along the shaft;
   (g) a coaxial guide bore on the gear, the coaxial guide bore being located on the side of the gear facing away from the motor;
   (h) a second lifting cam; and
   (i) a second cam follower, one of the second lifting cam and the second cam follower being located in the guide bore, and the other of the second lifting and the second cam follower being associated with the reciprocable rack such that when the gear is rotating, the guide bore rotates and causes a corresponding reciprocating motion of the reciprocable rack.

21. The cleaning device of claim 20, wherein the reciprocable rack is confined so as to not rotate relative to the housing of the cleaning device.

22. The cleaning device of claim 20, further comprising at least one radial guide pin associated with the reciprocable rack for movement therewith; and
   a longitudinal groove located in the housing of the cleaning device or the slip-on brush head assembly, the groove extending axially in the direction of the stroke of the reciprocable rack, the groove receiving the radial guide pin.

23. The cleaning device of claim 20, wherein the first lifting cam and the second lifting cam are oriented in opposing directions such that as the gear moves axially outward on the motor shaft relative to the motor, the reciprocable rack moves axially outward relative to the guide bore.

24. A cleaning device defining a longitudinal axis therethrough, the cleaning device comprising:
   (a) a housing comprising:
      a handle segment; and
      a slip-on head segment removably attached to the handle segment;
   (b) a motor shaft extending from the handle segment to the head segment and aligned substantially parallel to the longitudinal axis;

(c) a motor located in the handle segment for rotating the shaft about the longitudinal axis of the shaft;

(d) a reciprocable rack located in the head segment which extends substantially parallel to the longitudinal axis of the cleaning device;

(e) a cleaning head operatively connected with the reciprocable rack;

(f) a gear disposed in the slip-on head segment mounted for rotation with the shaft and for sliding movement along the shaft, the gear being operatively connected to the reciprocable rack so as to convert the rotation of the shaft into a reciprocating stroke of the rack;

(g) a lifting cam and a cam follower, one of the lifting cam and the cam follower positioned to rotate with the gear, the other of the lifting cam and the cam follower associated with the housing of the cleaning device, the cam follower interacting with the lifting cam such that when the gear is in the revolving motion of rotation, the gear oscillates back and forth along the shaft; and a coupling on the gear which, when the slip-on head segment is slid on the handle segment, couples with the motor shaft, which leads out of the handle segment.

* * * * *

UNITED STATES PATENT AND TRADEMARK OFFICE
CERTIFICATE OF CORRECTION

PATENT NO. : 5,383,242
DATED : January 24, 1995
INVENTOR(S) : Michael Bigler, et. al.

It is certified that error appears in the above-indentified patent and that said Letters Patent is hereby corrected as shown below:

In column 3, line 1, replace "pat" with -- part --.

In column 3, line 46, replace "shorn" with -- shown --.

Signed and Sealed this

Ninth Day of May, 1995

Attest:

BRUCE LEHMAN

*Attesting Officer*     *Commissioner of Patents and Trademarks*